United States Patent [19]

Neiss et al.

[11] Patent Number: 4,804,742

[45] Date of Patent: * Feb. 14, 1989

[54] AMIDE ANALOGS OF CALCITONIN

[75] Inventors: Edward S. Neiss, New Canaan, Conn.; David Stevenson, Scarsdale, N.Y.; Laurence L. Ho, New Rochelle, N.Y.; Robert C. Liu, White Plains, N.Y.; John T. Suh, Greenwich, Conn.

[73] Assignee: Rorer Pharmaceutical Corporation, Fort Washington, Pa.

[*] Notice: The portion of the term of this patent subsequent to Mar. 17, 2004 has been disclaimed.

[21] Appl. No.: 938,671

[22] Filed: Dec. 5, 1986

Related U.S. Application Data

[62] Division of Ser. No. 741,936, Jun. 6, 1985.

[51] Int. Cl.$^4$ .......................................... C07C 103/52
[52] U.S. Cl. .................................................... 530/307
[58] Field of Search ...................... 514/9, 11, 12, 808; 530/307

[56] References Cited

U.S. PATENT DOCUMENTS

| | | | |
|---|---|---|---|
| 3,798,203 | 3/1974 | Brugger et al. | 514/808 |
| 3,869,549 | 3/1975 | Geller | 514/12 |
| 3,934,008 | 1/1976 | Rittel et al. | 514/807 |
| 4,650,854 | 3/1987 | Neiss et al. | 530/307 |

OTHER PUBLICATIONS

*Peptides:* Synthesis-Structure-Function, Proceedings of the 7th American Peptide Symposium, Pierce Chemical Co., Rockford, Ill. 1981, pp. 131–134.

Foster et al., *Clinical Endocrinal. Metab.* 1/1, 93–124 (1972).

*Primary Examiner*—Johnnie R. Brown
*Assistant Examiner*—F. T. Moezie

[57] ABSTRACT

New peptides are disclosed which have biological activity of the same type as known calcitonins and which are amide analogs of natural calcitonins.

2 Claims, No Drawings

AMIDE ANALOGS OF CALCITONIN

This is a division of U.S. patent application Ser. No. 741,936, filed June 6, 1985.

FIELD OF THE INVENTION

This invention relates to amide analogs of calcitonin having biological activity and particularly having extended duration of activity.

BACKGROUND OF THE INVENTION

All known natural calcitonin peptides contain an amino acid sequence of 32 amino acids. Salmon calcitonin, for example, has the following formula:

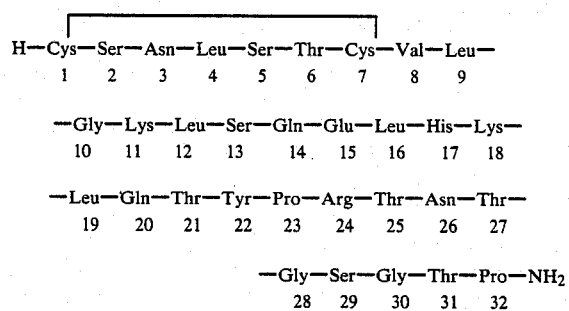

In U.S. Pat Nos. 3,926,938, 4,062,815, 3,929,758, 4,033,940 and 4,217,268 are disclosed improved syntheses of calcitonins including the salmon calcitonin referred to above.

The natural calcitonins include the salmon, eel, bovine, porcine, ovine and human calcitonins. For exemplification of the structures of the various calcitonins, see U.S. Pat. No. 4,422,967, Col. 3, which is hereby incorporated by reference.

SUMMARY OF THE INVENTION

We have discovered that amide analogs of calcitonin have biological activity of the same type as known calcitonins but with extended duration of activity.

Amide analogs of salmon calcitonin:

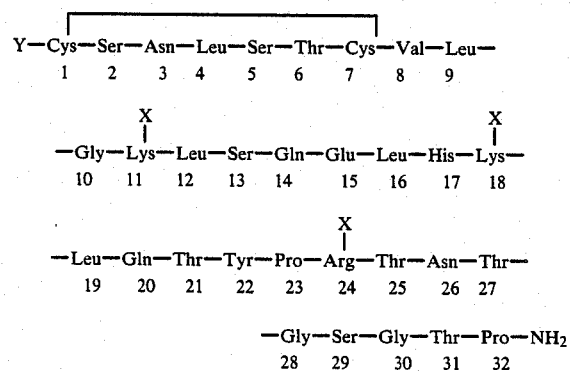

wherein X and Y are as defined below.

Amide analogs of eel calcitonin:

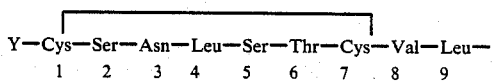

$$
\begin{array}{c}
\overset{X}{|} \\
-Gly-Lys-Leu-Ser-Gln-Glu-Leu-His-Lys- \\
10\ \ 11\ \ 12\ \ 13\ \ 14\ \ 15\ \ 16\ \ 17\ \ 18
\end{array}
$$

$$
\begin{array}{c}
\overset{X}{|} \\
-Leu-Gln-Thr-Tyr-Pro-Arg-Thr-Asp-Val- \\
19\ \ 20\ \ 21\ \ 22\ \ 23\ \ 24\ \ 25\ \ 26\ \ 27
\end{array}
$$

$$
-Gly-Ala-Gly-Thr-Pro-NH_2 \\
28\ \ 29\ \ 30\ \ 31\ \ 32
$$

wherein X and Y are as defined below.

Amide analogs of human calcitonin:

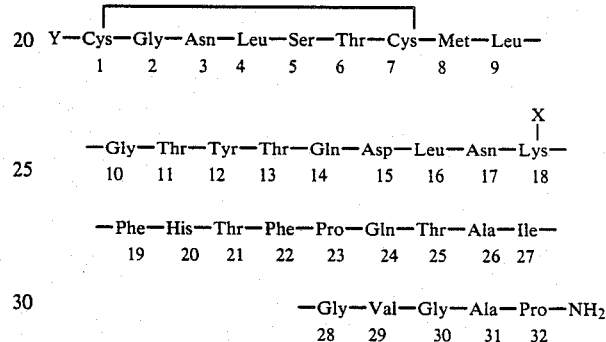

$$
-Phe-His-Thr-Phe-Pro-Gln-Thr-Ala-Ile- \\
19\ \ 20\ \ 21\ \ 22\ \ 23\ \ 24\ \ 25\ \ 26\ \ 27
$$

$$
-Gly-Val-Gly-Ala-Pro-NH_2 \\
28\ \ 29\ \ 30\ \ 31\ \ 32
$$

wherein X is H or a branched or linear alkanoyl having 2-20 carbon atoms, wherein the alkyl of alkanoyl may be substituted with a phenyl or hydroxy group and wherein Y is defined as X with the proviso that if all other X substitutions are H, Y is $C_8$–$C_{20}$ alkanoyl, wherein the alkyl of alkanoyl may be substituted with a phenyl or hydroxy group.

Included within the present invention are also the corresponding bovine, porcine, ovine and rat calcitonin analogs.

Monikawa et al. [Experientia, 32(9), 1104-1106 (1976)] showed that synthetic eel calcitonin has a hypocalcemic potency around 4300 Iu/mg., while the synthetic analog (1,7-α-L-aminosuberic acid)eel calcitonin has a hypocalcemic potency of about 3400 Iu/mg.

Therefore, we also include within the present invention the 32 amino acid analogs of salmon and eel calcitonin in which the first and seventh cysteines are replaced by α-L-aminosuberic acid and the amino groups have been acylated individually, severally or totally.

In addition, we also include analogs of all the aforementioned calcitonins where the L-lysine residues have been replaced by D-lysine, individually or totally and similar acylated or partially acylated compounds.

Orlowski, et al. (U.S. Pat. No. 4,469,632) has shown that if Arg (24) of salmon calcitonin is replaced by D-Arg, there is no significant loss of activity; the hypocalcemic potency is 5000 IU/mg. Therefore, we also include similar analogs of salmon or eel calcitonin to those already described where Arg (24) is replaced by D-Arg (24).

Approved human medical uses for salmon calcitonin include treatment of Paget's disease and osteoporosis.

DETAILED DESCRIPTION OF THE INVENTION

As may be seen from the formula given above, 32 amino acids are involved and in this formula the positions are numbered according to the accepted procedure beginning at position 1 for the Cys on one end of the chain, and ending with Pro at position 32 at the other end of the chain. For clarity of description, this same numbering system will be followed in referring to the cycles of the synthesis. The assembly of the amino acids begins with cycle 32 which involves the coupling of proline and continues with cycle 31 which involves the coupling of threonine, etc.

The amide analogs of calcitonin are formed at the peptide positions having a lysine or arginine, or at the cysteine at position one.

In salmon and eel calcitonin, lysines are at the 11 and the 18 positions and arginine is at the 24 position. Therefore, various mono, di, tri and tetra amides are possible.

In human calcitonin, lysine is only in the 18 position. Therefore, various mono and di amides are possible.

The alkanoyl of X may be straight-chained or branched and include acetyl, propanoyl, butanoyl, isobutanoyl, tert-butanoyl, 2,2-dimethylpropanoyl, dimethylbutanoyl, 2,5-dimethyloctanoyl, 2,2,6,6-tetramethyldecanoyl, 2,isopropylpentanoyl, 3,3-dimethylheptanoyl, dodecanoyl, 2,4-diethylundecanoyl, 2,2-dimethylpentanoyl, decanoyl, and pivalyl.

The alkyl of the alkanoyl may be substituted with a phenyl or hydroxy group.

Y is defined as X is above except if the other X substitutions are H when Y has a $C_8$–$C_{20}$ alkanoyl. The alkyl of this alkanoyl may also be substituted with a phenyl or hydroxy group.

Preferred compounds include:
N($\alpha$)-decanoyl-Cys(1) salmon calcitonin;
N($\epsilon$)-decanoyl-Lys(18) salmon calcitonin;
N($\alpha$)-decanoyl-Cys(1)-N($\epsilon$)-decanoyl-Lys(11)-N($\epsilon$)-decanoyl-Lys(18) salmon calcitonin;
N($\alpha$)-pivalyl-Cys(1)-N($\epsilon$)-pivalyl-Lys(11)-N($\epsilon$)-pivalyl-Lys(18) salmon calcitonin.
N($\alpha$)-decanoyl-Cys(1)-N($\epsilon$)-decanoyl-Lys(11)-N($\epsilon$)-decanoyl-Lys(18)-N($\omega$)-decanoyl-Arg(24) salmon calcitonin
N($\alpha$)-pivalyl-Cys(1)-N($\epsilon$)-pivalyl-Lys(11)-N($\epsilon$)-pivalyl-Lys(18)-N($\omega$)-pivalyl-Arg(24) salmon calcitonin

RESIN PEPTIDE SYNTHESIS

The amino acid chain sequence may be assembled by use of classical synthesis techniques or by solid phase techniques. For exemplification, the salmon calcitonin structure is used. However, these procedures can also be used for eel, human, bovine, porcine, ovine or any analogs of calcitonin.

Preferably, the peptide is assembled using solid phase synthesis. One can start with a resin called benzhydryl amine resin (BHA resin). This resin is derived from a cross-linked polystyrene bead resin manufactured by copolymerization of styrene and divinylbenzene. Resin of this type is known and its preparation is further demonstrated by Pietta et al. [Pietta, P. S. and Marshall, G. R., *Chem. Commun.*, 650 (1970)], and Orlowski et al., [*J. Org. Chem.*, 41, 3701 (1976)]. The cross-linked polystyrene BHA resin is available from chemical supply houses. The designation

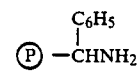

represents the BHA resin in which Ⓟ is the polystyrene portion of the resin.

Alternatively, one can start from a resin which is an amino-methyl resin instead of a BHA resin.

The assembly of the resin-peptide from amino-methyl resin preferably includes a step in which a "handle" of the type described by Gaehde and Matsueda (Int. J. Peptide Protein Res. 18, 451–458 (1981)) is incorporated between the resin and the terminal amino acid of the polypeptide. More preferably, norleucine is incorporated between the resin and the "handle" as an internal reference standard.

Thus, BOC-Nle is reacted with the resin in the presence of dicyclohexylcarbonyldiimide (DCCI) and hydroxybenzotriazole (HOBT) to form

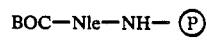

The BOC group is removed by adding acid to this product (such as HCl in dioxane or trifluoroacetic acid in toluene or in methylene chloride) and then neutralizing with e.g. diisopropylamine. Then the BOC-protected "handle",

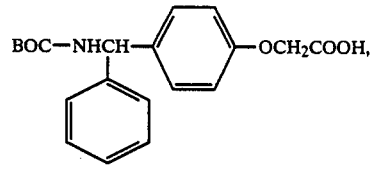

DCCI and HOBT are added to couple the BOC-handle to the deprotected norleucine residue. Following removal of the BOC group from the handle, by acidification and neutralization, cycle 32 begins in which BOC-proline is coupled to the deprotected nitrogen of the "handle".

In general, each amino acid is reacted with the resin peptide in a suitable solvent such as toluene, chloroform, methylene chloride, or dimethyl formamide, in the presence of a coupling agent, and subsequently deprotected with acid followed by a neutralizing step; then the next amino acid is added, and so forth.

The amino acids are added one at a time to the insoluble resin until the total peptide sequence has been built up on the resin. The functional groups of the amino acids are protected by blocking groups. The $\alpha$-amino group of the amino acids is protected by a tertiary butyloxycarbonyl group or an equivalent thereof. This $\alpha$-tertiary butyloxycarbonyl group we designate as BOC. The hydroxyl functions of serine and threonine are protected by a benzyl or benzyl derivative group such as 4-methoxybenzyl, 4-methylbenzyl, 3,4-dimethylbenzyl, 4-chlorobenzyl, 2,6-dichlorobenzyl, 4-nitrobenzyl, benzhydryl or an equivalent thereof. We use the term Bzl to represent the benzyl or benzyl derivative group.

The hydroxyl function of tyrosine may be unprotected, may be protected by a benzyl or benzyl derivative group as described above, as a Bzl group, or may be protected by a benzyloxycarbonyl or a benzyloxycarbonyl derivative such as 2-chlorobenzyloxycarbonyl or 2-bromobenzyloxycarbonyl group or equivalent thereof.

The thiol function of cysteine may be protected by benzyl or benzyl derivative protective groups described above and designated Bzl, and preferably p-methylbenzyl or p-methoxybenzyl; or by an alkylthio group such as methylthio, ethylthio, n-propylthio, n-butylthio, t-butylthio or equivalents thereof or another cysteine group. One cysteine, preferably Cys(7), is protected by Bzl and the other, preferably Cys(1), is protected by an alkylthio group. The guanidine function of arginine may be protected by a nitro group, a tosyl group or an equivalent thereof. The ε-amino function of lysine may be protected preferably by FMOC (9-fluorenylmethyloxycarbonyl) or by a benzyloxycarbonyl group or a benzyloxycarbonyl derivative such as a 2-chlorobenzyloxycarbonyl, 3,4-dimethylbenzyloxycarbonyl, or equivalents thereof. The protective groups used on the imidazole nitrogen of histidine are tosyl, benzyloxymethyl, or benzyloxycarbonyl. The γ-carboxylic acid group of glutamic acid is protected by a benzyl or benzyl derivative group such as described for the protection hydroxyl function of serine and threonine.

The invention will be described herein with particular reference to the synthesis of derivatives of salmon calcitonin.

As may be seen from the formula given above for salmon calcitonin, 32 amino acids are involved and in this formula the positions are numbered according to the accepted procedure beginning at position 1 for the Cys on one end of the chain, and ending with Pro at position 32 at the other end of the chain. For clarity of description, this same numbering system will be followed in referring to the cycles of the synthesis. The assembly of the amino acids of salmon calcitonin begins with cycle 32 which involves the coupling of proline and continues with cycle 31 which involves the coupling of threonine, etc.

Preferred amino acid reactants for use in each of the 32 cycles of the synthesis of salmon calcitonin derivatives of the present invention (used for exemplification only) are given in the following Table I:

TABLE I

| Cycle Number | Amino Acid Reactant |
|---|---|
| 32 | BOC-L-proline |
| 31 | BOC-O—benzyl-L-threonine |
| 30 | BOC-glycine |
| 29 | BOC-O—benzyl-L-serine |
| 28 | BOC-glycine |
| 27 | BOC-O—benzyl-L-threonine |
| 26 | BOC-L-asparagine |
| 25 | BOC-O—benzyl-L-threonine |
| 24 | BOC-ω-tosyl-L-arginine |
| 23 | BOC-L-proline |
| 22 | BOC-O—bromobenzyloxycarbonyl-L-tyrosine |
| 21 | BOC-O—benzyl-L-threonine |
| 20 | BOC-L-glutamine |
| 19 | BOC-L-leucine |
| 18 | BOC-ε-2-chlorobenzyloxycarbonyl-L-lysine or BOC-ε-decanoyl-L-lysine or BOC-ε-9-fluorenylmethyloxycarbonyl-L-lysine |
| 17 | BOC-N(im)—CBZ-L-histidine |
| 16 | BOC-L-alanine |
| 15 | BOC-L-glutamic acid γ-benzyl ester |
| 14 | BOC--glutamine |
| 13 | BOC-O—benzyl-L-serine |
| 12 | BOC-L-leucine |
| 11 | BOC-ε-2-chlorobenzyloxycarbonyl-L-lysine or BOC-ε-decanoyl-L-lysine or BOC-ε-9-fluorenylmethyloxycarbonyl-L-lysine |
| 10 | BOC-glycine |

TABLE I-continued

| Cycle Number | Amino Acid Reactant |
|---|---|
| 9 | BOC-L-leucine |
| 8 | BOC-L-valine |
| 7 | BOC-S—p-methoxybenzyl-L-cysteine, BOC-S—3,4-dimethylbenzyl-L-cysteine or BOC-S—p-methylbenzyl-L-cysteine |
| 6 | BOC-O—benzyl-L-threonine |
| 5 | BOC-O—benzyl-L-serine |
| 4 | BOC-L-leucine |
| 3 | BOC-L-asparagine |
| 2 | BOC-O—benzyl-L-serine |
| 1 | BOC-S—ethylthio-L-cysteine, BOC-S—methylthio-L-cycsteine, BOC-S—n-propylthio-L-cysteine or BOC-S—n-butylthio-L-cysteine |

Each of the amino acid derivatives mentioned in Table I may be purchased from supply houses with the exception of BOC-ε-decanoyl-L-lysine.

A process for making BOC-ε-decanoyl-L-lysine is as follows:

PREPARATION OF SUCCINIMIDYL n-DECANOATE n-Decanoyl chloride, 13.4 g, 70 mmoles was dissolved in methylene chloride, 350 ml. The mixture was chilled to −5°–0° C. in a salt-ice bath. With concomitant stirring and cooling, the potassium salt of N-hydroxipuccinimide, 15.3 g, 100 mmoles was added to the solution in portions such that the temperature did not exceed 5° C. The mixture was stirred at room temperature for a further two hours, after which the insoluble potassium chloride was filtered off. The filtrate was evaporated to dryness and the residue dissolved in ethyl acetate. The solution was washed with water, dried over magnesium sulfate and evaporated. Trituration of the residue with ether afforded a white crystalline solid, 21.7 g (90% of theory), m.p. 63° C. The NMR and mass spectra were consistent with the structure.

Preparation of BOC ε-decanoyl-L-lysine

BOC-L-Lysine, 2.46 g, 10 mmoles was suspended in DMF, 50 ml. To this was added tetramethylguanidine, 3.5 ml and the whole mixture was heated to 40–50° C. until a homogeneous solution was obtained. Succinimidyl n-decanoate, 4 g, 15 mmoles, was added portionwise such that the temperature did not exceed 50° C. The solution was left overnight at room temperature. The DMF was removed in vacuo and the residue was partitioned between ethyl acetate and 0.5N sulfuric acid. The organic extract was washed successively with 0.5N sulfuric acid and water, dried (MgSO₄) and evaporated to give a yellowish oil.

This oil was dissolved in methylene chloride, 10 ml. To this was added N sodium hydroxide solution, 15 ml, plus water, 10 ml. After shaking vigorously, the organic layer was separated and discarded. The aqueous layer was washed with methylene chloride and then was acidified with 0.5N sulfuric acid. The desired product separated as an oil. This was extracted into ethyl acetate, washed successively with water and saturated sodium chloride solution, dried (MgSO₄) and evaporated to a colorless oil, which slowly crystallized when triturated with hexane. The crude solid was recrystallized from ether-hexane to afford 3.63 g product, 91% of theory, m.p. 73° C. The NMR and mass spectra were consistent with the structure.

EXAMPLE 1

N(α)decanoyl-Lys(18) salmon calcitonin

Neutralization of Amino-methyl resin

An 11.0 g sample of aminomethyl resin hydrochloride, corresponding to approximately 10 mmoles amine groups (i.e. with a substitution of 0.9 milliequivalents of amine groups per gram of resin) was placed in the reaction vessel of a Vega Model 50 Peptide Synthesizer (Vega Biochemicals, Division of Vega Laboratories Inc., P.O. Box 11648, Tucson, Ariz. 85734). The resin was swollen by shaking in methanol (150 ml) for five minutes and then was washed with methylene chloride (3×150 ml, 1 minute each) and with 15% methanol in methylene chloride (150 ml) for one minute. It was treated with 5% di-isopropylamine (DIA) in methylene chloride (150 ml) for 1 minute. It was washed once with 15% methanol in methylene chloride (150 ml, 1 minute) then retreated with 5% DIA in methylene chloride (150 ml, 1 minute). This washing and base treatment was repeated and then the resin was washed six times with methylene chloride (150 ml, 1 minute each).

Removal of α-BOC Group

This was performed using 50% v/v trifluoroacetic acid in methylene chloride, preferably in the presence of 2% v/v 2-mercaptoethanol.

The BOC-protected resin is treated as follows:

| | | |
|---|---|---|
| Methylene chloride + 2% v/v 2-mercaptoethanol | 3 × 150 ml | 1 minute |
| 50% v/v TFA in methylene chloride + 2% v/v 2-mercaptoethanol | 2 × 150 ml | 1 × 1 min., 1 × 30 min. |
| Methylene chloride + 2% v/v 2-mercaptoethanol | 3 × 150 ml | 1 minute |
| Methanol (15% v/v) in methylene chloride | 6 × 150 ml | 1 minute |
| Di-isopropylamine (5% v/v) in methylene chloride | 2 × 150 ml | 1 minute |
| Methanol (15% v/v) in Methylene Chloride | 3 × 150 ml | 1 minute |
| Di-isopropylamine (5% v/v) in methylene chloride | 1 × 150 ml | 1 minute |
| Methylene Chloride | 6 × 150 ml | 1 minute |

Addition of N-Boc-p-(α-aminophenylmethyl)phenoxyacetic acid, the "handle"

To the neutralized resin, containing 10 mmoles amino groups, was added the acylating solution containing 20 mmoles of the title compound. This acylating solution was prepared by dissolving the title compound (7.14 g, 20 mmoles) and 1-hydroxybenzotriazole, HOBT, (3.9 g, 25 mmoles) in dimethyl acetamide, 45 ml. To this was added methylene chloride, 100 ml, and the solution was cooled to 0°–5° C. 10 ml of a solution of 2M dicyclohexylcarbodiimide, DCCI, in toluene were added and the mixture was kept at room temperature for 30 minutes. Dicyclohexylurea was filtered off and the filtrate added to the resin.

The mixture was shaken overnight for convenience, although a coupling time as short as one hour would be adequate. The resin was drained and washed for one minute each time with three 150 ml portions of methylene chloride, six 150 ml portions of methanol and six 150 ml portions of methylene chloride. A ninhydrin test [Kaiser et al, Anal. Biochem. 34, 595-8 (1969)] was performed and on all but one occasion was found to be negative. If it should have been even slightly positive, recoupling would have been performed or the resin would have been acetylated. On the occasion that one bead was dark, acetic anhydride, 15 ml, pyridine, 15 ml and methylene chloride, 150 ml, were shaken with the resin for fifteen minutes. The resin was washed as just described for the coupling reaction.

Addition of Pro 32, Thr 31, Gly 30, Ser 29, Gly 28, Thr 27, Asn 26, Thr 25, Arg 24

In general, each of these residues was incorporated as described for the "handle" and the BOC groups were removed similarly using TFA.

Completeness of coupling of Thr (31) to Pro (32) and of Tyr (22) to Pro (23) was monitored by the isatin test (Kaiser E., Bossinger C. D., Colescott, R. L. and Olsen, D. B., Analytica Chimica Acta., 118, 149 (1980)).

Addition of Pro (23), Tyr (22), Thr (21), Gln (20), Leu (19), Lys (18)

In general, each of these residues was incorporated as described for the "handle" except that dimethyl formamide was used for the coupling solvent. The BOC group was removed using TFA.

Addition His (17)

The acylating solution was prepared as for the "handle" but using dimethyl formamide as solvent. However, after adding the solution of DCCI in toluene, the cold solution was added immediately to the resin.

Addition of all other residues

In general, each of these residues is incorporated as described for the "handle" except that dimethyl formamide is used for the coupling solvent. After Cys(7) is added, it is essential that 2-mercaptoethanol be present during acid deblocking treatments.

In the above, Lys (18) is protected with decanoyl and Lys (11) with the ε-2-chloro-benzyloxycarbonyl group.

After incorporation of Cys (1), the BOC group is not removed, but is left on to be removed during HF cleavage.

Addition of Lys (11) using ε-FMOC and all subsequent residues

Acylating solutions are prepared as described for the "handle" but dimethyl acetamide is preferred as coupling solvent.

The preferred method for deblocking is to use TFA and for neutralization, all di-isopropylamine in methylene chloride treatments were replaced by 5% v/v triethylamine in methylene chloride treatments, and each of these were for only ten seconds.

After incorporation of Cys (1), the BOC group is not removed with TFA but is left on, to be removed during the HF cleavage. As FMOC is being used, this must be removed before HF cleavage, for instance using this procedure:

Treat the resin as follows:

| | |
|---|---|
| wash with DMF | 3 × 1 min. × 150 ml |
| 10% Piperidine in DMF | 1 × 1 min., 1 × 15 min. 200 ml each |
| DMF | 3 × 1 min. × 150 ml |
| CH$_2$Cl$_2$ | 6 × 1 min. × 150 ml |

Cleavage of Resin Peptide with Hydrogen Fluoride

The dried resin peptide (2 g.) and 2 ml. of m-cresol and 2 ml of 1,2-ethanedithiol were placed in a Teflon reaction vessel. The vessel equipped with a Teflon-coated magnet stirrer was placed in a liquid nitrogen or dry ice-acetone bath and 10 ml. of hydrogen fluoride gas was condensed into the vessel. This mixture was stirred at 0 degrees centigrade in an ice bath for 1 hour.

The hydrogen fluoride was removed by evaporation at reduced pressure. The residue was triturated with six 25 ml. portions of ethyl acetate. The residue was dried in vacuo.

Cyclization Of The Peptide

The resin peptide mixture obtained from hydrogen fluoride cleavage was mixed with 1000 ml of distilled water. The pH of the solution was adjusted to 8.5 by the addition of concentrated ammonium hydroxide. The solution was stirred in a closed vessel under a stream of nitrogen for 20 hours. At this time no ethyl mercaptan could be detected in the emerging nitrogen stream. The ethyl mercaptan content of the nitrogen stream was measured by passing the stream through a solution of Ellman's reagent [Ellman, G. L., *Arch. Biochem. Biophys.*, 82, 70–7 (1969)]. The pH of the reaction mixture was adjusted to 4.0 by addition of glacial acetic acid and freeze-dried affording a fluffy solid.

Purification Of The Crude ϵ-decanoyl-Lys(18)-SCT

The fluffy solid from the above synthesis was dissolved in a small amount of 0.5N acetic acid and purified by passing through a Sephadex G-25 (fine) gel-filtration column and eluting with 0.5 molar aqueous acetic acid solution. The decanoyl-Lys(18)-SCT fraction from this column was freeze-dried and the resulting fluffy solid dissolved in ammonium acetate solution. This solution was further purified by ion-exchange chromatography using a Whatman CM-52 column eluted with ammonium acetate buffer. The peptide fraction was collected and freeze-dried. The product was further purified by preparative isocratic high performance liquid chromatography using a Zorbax $C_8$ column and the solvent system: 0.1% of trifluoroacetic acid in $H_2O$/acetonitrile (50/50, v/v). The fractions containing the product were combined and the acetonitride moved by evaporation. The product was recovered by lyophilization.

The product was obtained as a fluffy white solid and proved to be over 95% homogeneous by both molecular exclusion and reverse phase HPLC methods.

EXAMPLE 2

Preparation of
N(α)-Decanoyl-Cys(1)-N(ϵ)-Decanoyl-Lys(11)-N(ϵ)-Decanoyl-Lys(18)-Lys(11)-N(ϵ)-Decanoyl-Lys(18)-Salmon Calcitonin Salmon calcitonin, 100 mg, (approx. 0.03 mM) was dissolved in 5 ml of water and the pH was adjusted to 7.0 with phosphate buffer. This solution was chilled to 0°–5° C. in an ice-bath. To this solution was added a solution of 80 mg (0.3 mM) of N-hydroxysuccininide n-decanoate in 2 ml of tetrahydrofuran. The mixture was kept stirring at 0° C. for 20 hours and at room temperature for an additional 5 hours. A small amount of solid sodium bicarbonate was added to maintain the pH of the mixture at 7–8. At the end of this period, no starting salmon calcitonin could be detected by T.L.C., and the mixture was freeze-dried. The residue was taken up in 5 ml of 25% acetic acid and purified by passing through a Sephadex G-25 (fine) column eluting with 25% aqueous acetic acid. The peptide fractions were combined and freeze-dried. The product was obtained as a fluffy white solid.

EXAMPLE 3

Preparation of N(α)-Decanoyl-Cys(1)-Salmon Calcitonin

This compound was prepared by solid phase peptide synthesis using methods similar to N(ϵ)-decanoyl-Lys(18)-SCT, but using ϵ-2-chlorobenzyloxycarbonyl for protection of Lys(18). After completion of the peptide sequence, the BOC group was removed from Cys(1). n-Decanoic acid was coupled onto Cys(1) in the standard way using DCCI/HOBT. The subsequent HF-cleavage, cyclization and purification, were also performed as described in the previous secitons for N(ϵ)-decanoyl-Lys(18)-SCT.

EXAMPLE 4

Preparation of
N(ϵ)-Pivalyl-Cys(1)-N(ϵ)-Pivalyl-Lys(11)-N(ϵ)-Pivalyl(18)-Salmon Calcitonin This compound was prepared as for the corresponding tridecanoyl substituted salmon calcitonin except that N-hydroxysuccinimide pivalate was utilized as acylating agent. Purification was performed by gel-filtration on Sephadex G-25 exactly as for the tridecanoyl analog.

What is claimed is:

1. N(α)-pivalyl-Cys(1)-N(ϵ)-pivalyl-Lys(11)-N(ϵ)-pivalyl-Lys(18) salmon calcitonin.

2. N(ϵ)-decanoyl-Lys(18) salmon calcitonin.

* * * * *